United States Patent
Herzog

Patent Number: 5,974,613
Date of Patent: Nov. 2, 1999

[54] BRUSH SECTION FOR AN ELECTRIC TOOTHBRUSH

[75] Inventor: Karl Herzog, Frankfurt, Germany

[73] Assignee: Braun Aktiengesellschaft, Frankfurt am Main, Germany

[21] Appl. No.: 08/837,905

[22] Filed: Apr. 22, 1997

Related U.S. Application Data

[63] Continuation of application No. PCT/EP96/01061, Mar. 13, 1996.

[30] Foreign Application Priority Data

Apr. 1, 1995 [DE] Germany .................. 195 12 318

[51] Int. Cl.[6] .................................. A61C 17/22
[52] U.S. Cl. ................... 15/22.1; 15/22.4; 15/28
[58] Field of Search .................. 15/22.1, 22.4, 15/28

[56] References Cited

U.S. PATENT DOCUMENTS

| | | | |
|---|---|---|---|
| 1,517,320 | 12/1924 | Stoddart | 15/22.1 |
| 1,997,730 | 4/1935 | Hite | 15/28 |
| 3,757,419 | 9/1973 | Hopkins | 15/28 X |
| 3,822,432 | 7/1974 | Skinner | 15/28 X |
| 3,935,869 | 2/1976 | Reinsch | 15/22.1 X |
| 4,603,448 | 8/1986 | Middleton et al. | 15/22.1 |
| 5,259,083 | 11/1993 | Stansbury, Jr. | 15/22.1 |
| 5,416,942 | 5/1995 | Baldacci et al. | 15/22.1 |

FOREIGN PATENT DOCUMENTS

| | | |
|---|---|---|
| 39 37 850 | 5/1991 | Germany . |
| 42 39 251 | 5/1994 | Germany . |
| 43 43 103 | 6/1995 | Germany . |

*Primary Examiner*—Mark Spisich
*Attorney, Agent, or Firm*—Fish & Richardson P.C.

[57] ABSTRACT

The invention is directed to a brush section (1) for an electric toothbrush which includes a mounting tube (2) in which a shaft (7) rotatably mounted about a longitudinal axis (3) and driveable in an oscillatory or rotary fashion is received. Further, the brush section (1) includes a bristle carrier (11) which is pivotally mounted on an angled end (19) of the shaft (7) configured as crankshaft and which, in operation of the electric toothbrush, is set in a rotary motion (26) about the transverse axis (14) by a pin (23). The angle (20) formed by the longitudinal axis (3) and the angled end (19) of the shaft (7) serves the added function of causing the bristle carrier (11) to perform a pivotal motion (27) about an axis (28).

12 Claims, 3 Drawing Sheets

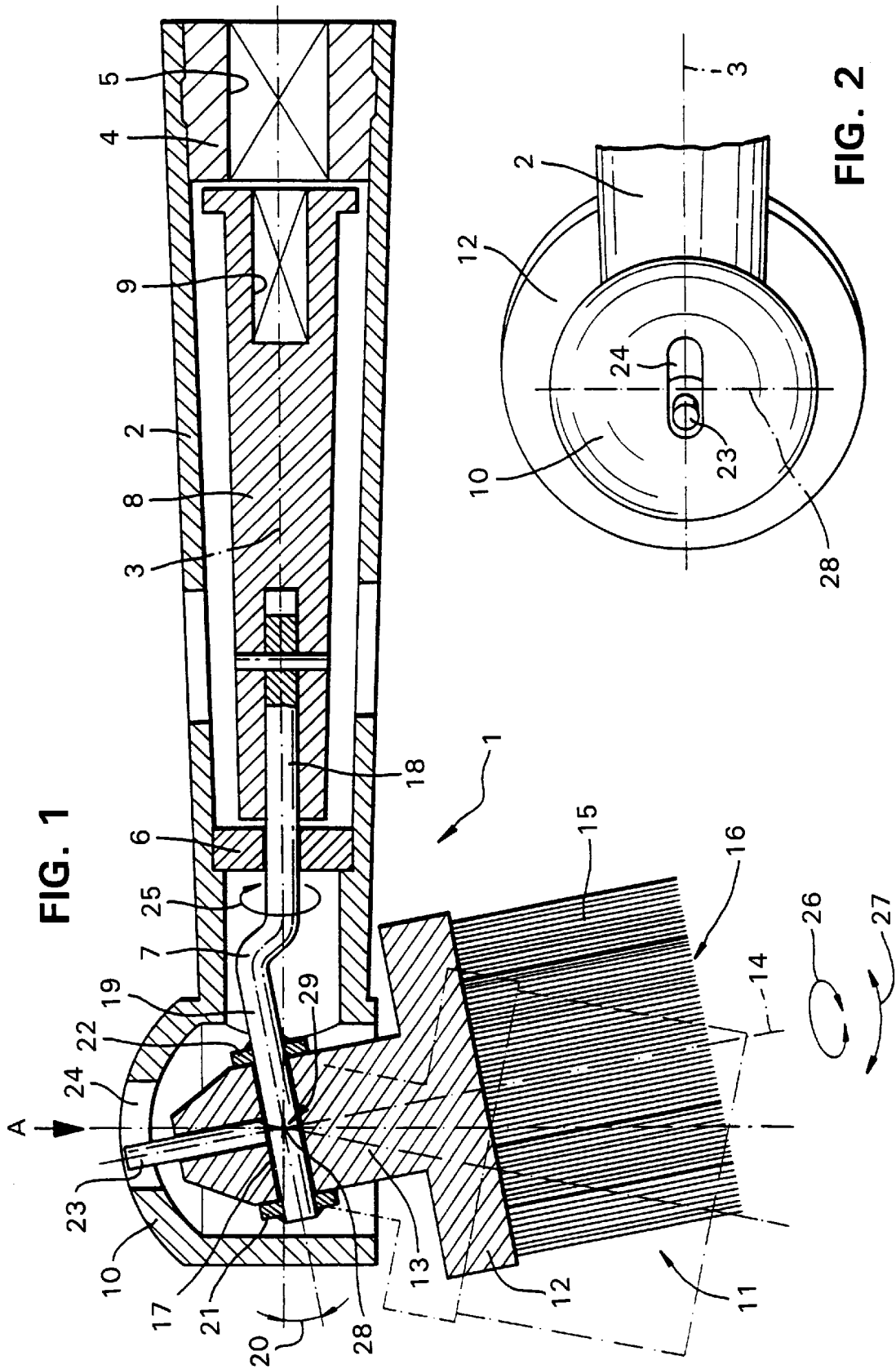

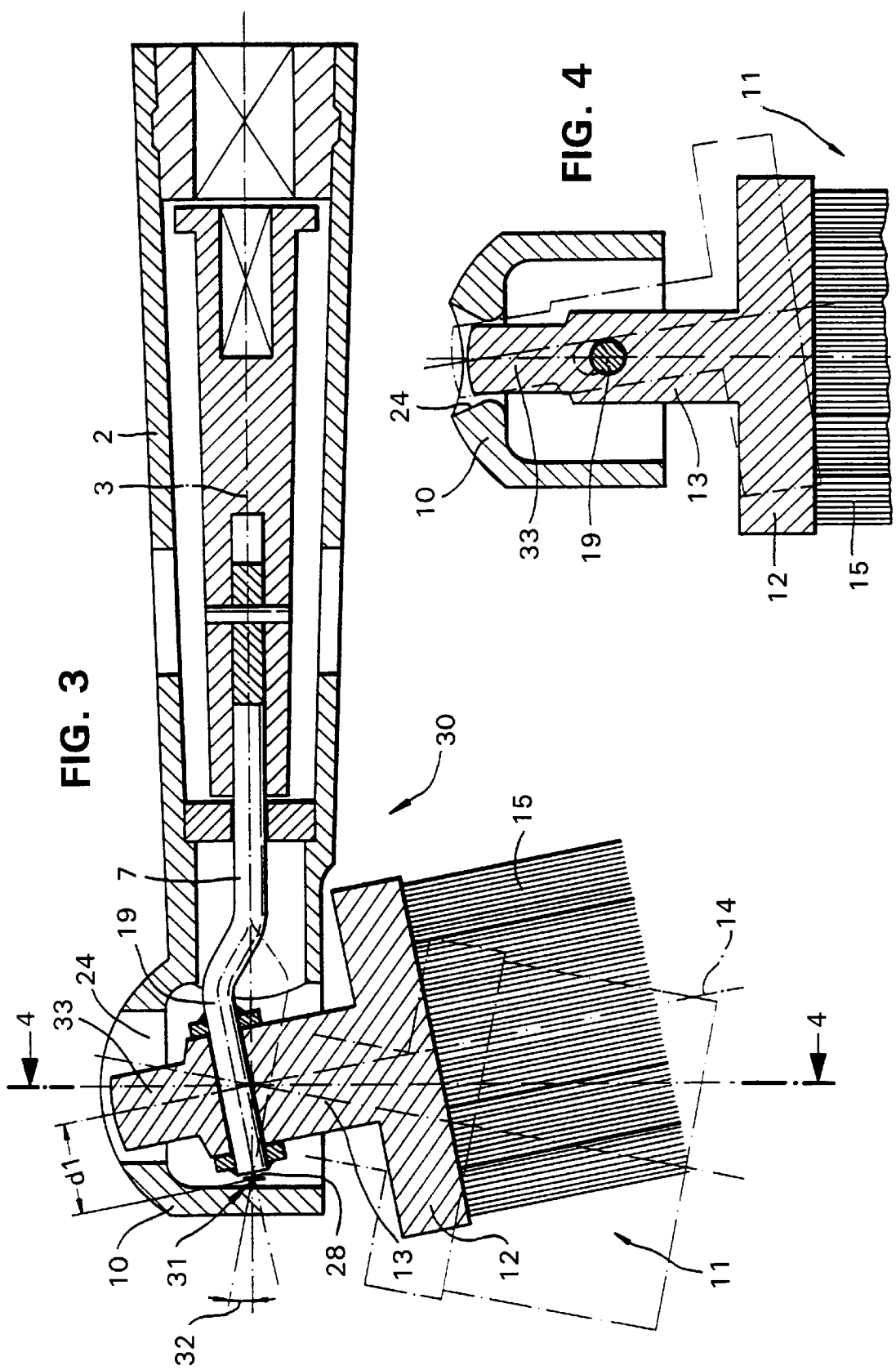

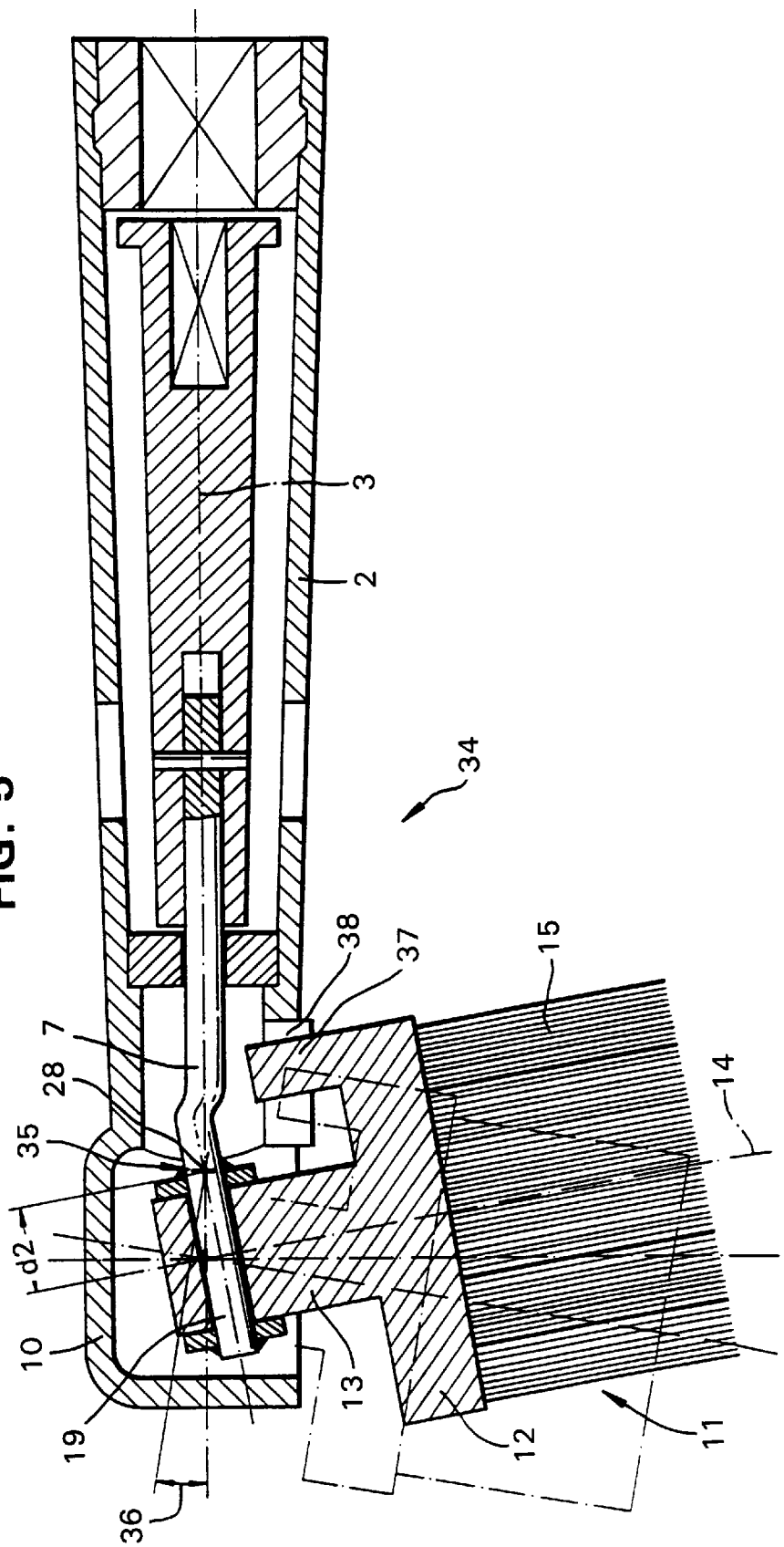

BRUSH SECTION FOR AN ELECTRIC TOOTHBRUSH

This application is a continuation of co-pending PCT/EP/96/01061, filed Mar. 13, 1996.

DESCRIPTION

This invention relates to electric toothbrushes and particularly to a brush section for an electric toothbrush.

A brush section of this type is known from German Offen-legungsschrift DE 39 37 850 A1 which is hereby incorporated in the disclosure content of the present patent application by express reference. In this specification, an electric toothbrush is described which has a handle section from which a drive shaft projects outwardly. The handle section receives in its interior electric drive means with the aid of which the drive shaft can be set in an oscillatory rotational motion about its longitudinal axis. A brush section extending in the direction of the longitudinal axis and having a mounting tube with a bristle carrier arranged at its end is adapted to be push-fitted onto the handle section and the drive shaft. The mounting tube accommodates in its interior a shaft which, when push-fitted, is coupled to the drive shaft. Extending from the bristle carrier is a plurality of bristles which are arranged at approximately right angles to the longitudinal axis of the brush section. By means of a bevel gear arrangement, the oscillatory rotational motion transmitted by the drive shaft to the shaft of the brush section is deflected by about 90 degrees. As a result, with the electric toothbrush activated, the bristle carrier executes an oscillatory rotational motion about an axis which is approximately at right angles to the longitudinal axis of the brush section and thus approximately parallel to the bristles. The cleansing face formed by the free ends of the bristles thus performs an oscillatory rotational motion on a user's tooth surfaces. This oscillatory rotational motion is apt to produce a good cleaning action on the tooth surfaces.

It is an object of the present invention to provide a brush section for an electric toothbrush which includes a simple drive mechanism and with which an improved dental cleaning operation can be accomplished.

Embodiments of the invention may be characterized by a straightforward construction of the drive mechanism and a low number of components utilized, offering the prerequisite for setting the brush section in a rotary motion such as to permit an improved dental cleaning action.

In an advantageous further aspect of the present invention, a crankshaft is provided by means of which the additional pivotal motion of the bristle carrier is effected. This is a particularly simple and economical possibility in particular with regard to the manufacture of the brush section.

Particularly suitably, the angle formed by the crankshaft has a value ranging from 0 to 30 degrees, approximately. This range has proven particularly advantageous in practice, with an angle of ten degrees, approximately, being preferred.

In another advantageous further aspect of the present invention, the bristle carrier is mounted on the angled end of the crankshaft. For mounting, a bore in the bristle carrier is essentially sufficient. This is a particularly simple and hence economical solution especially with regard to manufacture.

In a particularly advantageous embodiment of the present invention, the longitudinal axis, the transverse axis, the angled end of the crankshaft and the axis pass through a common point of intersection. This results in a particularly well balanced curve-shaped spatial motion of the free ends of the bristles of the bristle carrier.

In another embodiment of the present invention, the longitudinal axis, the axis and the angled end of the crankshaft pass through a common point of intersection through which the transverse axis does not pass however. This enables other curve-shaped spatial motions of the free ends of the bristles of the bristle carrier to be accomplished. In this arrangement, it is particularly advantageous that the selection of different points of intersection enables different curve-shaped motions to be produced, each affording special advantages of its own.

In another advantageous embodiment of the present invention, the longitudinal axis and the end of the crankshaft are in parallel arrangement to each other.

In an advantageous further aspect of the present invention, a pin, a trunnion or the like projects from the bristle carrier and is coupled to a guiding structure, in particular a slot or the like. The cooperative relationship between the pin or trunnion and the slot prevents uncontrolled motions of the bristle carrier on a rotary motion of the crankshaft.

As a result of the additional pivotal motion of the bristle carrier, the cleansing face formed by the bristles' free ends performs an oscillatory pivotal motion in addition to the oscillatory rotational motion. As heretofore, the rotary motion effects a good cleaning action on a user's tooth surfaces. By means of the pivotal motion of the cleansing face, an improved dental cleaning action can be accomplished by reason of the additional component of motion.

The orientation of the axis provided for the additional pivotal motion has the result that the bristle carrier executes an additional reciprocal motion in the direction of the longitudinal axis of the bristles. This motion enhances the cleaning effect on the tooth surfaces. This improved dental cleaning effect is accomplished without any additional measures being taken by the user, that is, automatically.

A solution affording a particularly straightforward construction results by providing the shaft with an angled end onto which the bristle carrier is plugged. In this arrangement, the rotary motion of the crankshaft may be preferably continuous or, alternatively, oscillatory.

Further features, advantages and application possibilities of the present invention will become apparent from the subsequent description of embodiments illustrated in more detail in the accompanying drawings. It will be understood that any single feature and any combination of single features described and/or represented by illustration form the subject-matter of the present invention, irrespective of their summary in the claims and their back-reference.

In the drawings,

FIG. 1 is a schematic longitudinal sectional view of a brush section for an electric toothbrush utilizing a first embodiment of the invention;

FIG. 2 is a schematic top plan view of the brush section of FIG. 1 as seen looking from the direction A in FIG. 1;

FIG. 3 is a schematic longitudinal sectional view of a brush section for an electric toothbrush utilizing a second embodiment of the invention;

FIG. 4 is a schematic cross-sectional view, taken along the plane 4—4 of FIG. 3, of the bristle carrier of the brush section of FIG. 3;

FIG. 5 is a schematic longitudinal sectional view of a brush section for an electric toothbrush utilizing a third embodiment of the invention;

The brush sections described in the following with reference to FIGS. 1 to 6 are suited to operate in conjunction with an electric toothbrush of the type described in German Offen-legungsschrift DE 39 37 850 A1 and as hereby incorporated in the disclosure content of the present patent application by express reference. This electric toothbrush includes a handle section from which a drive shaft projects outwardly. The drive shaft and that end of the handle section from which the drive shaft projects have their outer surfaces contoured for push-fitting engagement with a brush section and for transmission of the rotary motion produced.

Accommodated inside the handle section are electric drive means which, on power on, set the drive shaft in rotation about its longitudinal axis. Using the brush sections described in German Offen-legungsschrift DE 39 37 850 A1, this is an oscillatory rotational motion about the longitudinal axis of the drive shaft, with the angular range swept in rotation being +/−35 degrees, approximately.

In like manner the brush sections described in the following with reference to FIGS. 1 to 7 are suited to operate in conjunction with an electric toothbrush of the type described in German Offen-legungsschrift DE 39 37 850 A1, but in which a continuous rotary motion of the drive shaft about its longitudinal axis is provided in lieu of the oscillatory rotational motion of the drive shaft.

FIGS. 1 and 2 illustrate as a first embodiment a brush section 1 which may be push-fitted onto the handle section and the drive shaft of the electric toothbrush initially referred to. The brush section 1 includes a mounting tube 2 extending in the direction of a longitudinal axis 3. At its free end close to the handle section, the mounting tube 2 has a profile ring 4 with an inside contour 5 complementary with the outside contour of the handle section. In this manner, the brush section 1 can be push-fitted onto the handle section in a manner preventing relative rotation.

At its end remote from the handle section, the mounting tube 2 has a bearing 6 in which a shaft 7, preferably made of metal, is mounted for rotation. The shaft 7 extends from the bearing 6 in the direction close to the handle section approximately up to the center of the mounting tube 2, while projecting in the direction remote from the handle section a length beyond the bearing 6 and thus beyond the mounting tube 2. In the direction close to the handle section, the shaft 7 is fixedly coupled, as by a cross pin, to another shaft 8 arranged in the longitudinal axis 3 and preferably fabricated from a plastic. The second shaft 8 has at its free end close to the handle section an inside contour 9 complementary with the outside contour of the drive shaft projecting outwardly from the handle section. This enables the drive shaft to be coupled to the second shaft 8 and hence also to the shaft 7 in a manner preventing relative rotation.

The inside and outside contours 5, 9 may be of a square, stellate or similar configuration when viewed in cross section, which are conformed to each other such as to enable a user to push and pull the brush section 1 onto and, respectively, off the handle section with ease, while at the same time secure seating of the brush section 1 on the handle section is also ensured.

At its end remote from the handle section, the mounting tube 2 has a cap structure 10 covering approximately the area in which the shaft 7 projects beyond the bearing 6 and thus beyond the mounting tube 2. Further arranged in this area are a bristle carrier 11 as well as means for coupling the bristle carrier 11 to the shaft 7 and to the mounting tube 2.

The bristle carrier 11 includes a disk-shaped plate 12 and a hub 13 and is essentially rotationally symmetrical to a transverse axis 14. On its side facing away from the shaft 7, the plate 12 has a plurality of bristles 15 extending from the plate 12 in a direction approximately parallel to the transverse axis 14. The bristles 15 are all of about equal length so that their free ends form an approximately circular cleansing face 16. It will be understood, of course, that cleansing faces of different appearance may be provided, such as profiled and/or slanting faces obtained by reason of different bristle lengths.

Arranged on the side of the plate 12 close to the shaft 7 is the hub 13 which includes a through bore 17 therein aligned at right angles to the transverse axis 14.

The shaft 7 is configured as a crankshaft. The end 18 of the shaft 7 close to the handle section is disposed in the longitudinal axis 3. The end 19 of the shaft remote from the handle section is arranged at an angle thereto. An angle 20 is formed between the end 19 of the shaft 7 and the longitudinal axis 3.

The angled end 19 of the shaft 7 is passed through the bore 17 in the bristle carrier 11. To prevent the bristle carrier 11 from slipping back and forth on the angled end 19 of the shaft 7, a respective disk 21, 22 is provided on either side of the bristle carrier 11 and fixedly connected with the angled end 19 of the shaft 7 as by welding. As a result, the bristle carrier 11 is pivotally mounted on the angled end 19 of the shaft 7.

A pin 23 is fixedly connected with the hub 13 of the bristle carrier 11 as by press-fitting. It is also possible for the pin to be integrally formed with the hub 13. The pin 23 is disposed in the transverse axis 14 and is thus normal to the direction predetermined by the angled end 19 of the shaft 7. In the cap structure 10 affixed to the mounting tube 2 is a slot 24 whose middle plane extends parallel to or in the longitudinal axis 3. The width of the slot 24 is slightly larger than the diameter of the pin 23, the length of the slot 24 depending, among other factors, from the value of the angle 20. The length of the pin 23 is selected such that it projects at least into the slot 24 and is thus guided by the slot 24.

When the electric toothbrush is in operation, the drive shaft projecting outwardly from the handle section imparts to the shaft 7 of the brush section 1 push-fitted to the handle section either an oscillatory or a continuous rotary motion about the longitudinal axis 3 as initially described. In the present embodiment, the shaft 7 is set in a rotary motion 25 about the longitudinal axis 3.

Both possible rotary motions, that is, the continuous as well as the oscillatory rotary motion, cause the free ends of the bristles 15 to perform curve-shaped motions. By reason of the guiding of the pin 23 in the slot 24, these spatial motions are composed of an oscillatory rotational motion 26 of the bristle carrier 11 about the transverse axis 14 on the one hand, and of an oscillatory rotational motion 27 of the bristle carrier 11 about an axis 28 on the other hand. The angular range of the oscillatory rotational motions 26, 27 is double the angle 20.

The axis 28 is arranged at an angle of 90 degrees, approximately, to the transverse axis 14 and 90 degrees, approximately, to the longitudinal axis 3. In the first embodiment, the longitudinal axis 3 and the angled end 19 of the shaft 7 intersect in a common point of intersection 29 through which also the axis 28 and the transverse axis 14 extend. The point of intersection 29 formed by the aforementioned axes is further intersected by the axis of the pin 23.

The cleansing face 16 of the bristle carrier 11 is thereby caused to perform an oscillatory rotational motion 26 about the transverse axis 14 while at the same time the complete cleansing face 16 executes a reciprocal motion about the axis 28.

In FIGS. 3 and 4, a second embodiment of a brush section 30 is shown which is adapted to be plugged onto the handle section and the drive shaft of the electric toothbrush initially explained. In contrast to the brush section 1 of the first embodiment in which the longitudinal axis 3, the angled end 19 of the shaft 7, the transverse axis 14 and the axis 28 pass through the common point of intersection 29, the brush section 30 of the second embodiment has a point of intersection 31 through which the longitudinal axis 3, the angled end 19 of the shaft 7 and the axis 28 pass but which is not coincident with the transverse axis 14. This point of intersection 31 is arranged on the side of the hub 13 of the bristle carrier 11 remote from the mounting tube 2. A distance d1 exists between the axis 28 and the axis 14.

In operation of the electric toothbrush, the second embodiment results in curve-shaped spatial motions of the free ends of the bristles 15 which differ from the spatial motions of the first embodiment.

Furthermore, the pin 23 press-fitted into the hub 13 in the first embodiment is replaced in the second embodiment of FIGS. 3 and 4 by a trunnion 33 integrally formed with the hub 13, said trunnion projecting into, and being accordingly guided by, the slot 24 in a manner similar to the pin 23. In this arrangement, the special form and contour of the slot 24 may differ as required.

FIG. 5 illustrates a third embodiment of a brush section 34 suitable to be plugged onto the handle section and the drive shaft of the electric toothbrush initially explained. In contrast to the brush section 1 of the first embodiment in which the longitudinal axis 3, the angled end 19 of the shaft 7, the transverse axis 14 and the axis 28 pass through the common point of intersection 29, the brush section 34 of the third embodiment has a point of intersection 35 through which the longitudinal axis 3, the angled end 19 of the shaft 7 and the axis 28 pass but which is not coincident with the transverse axis 14. This point of intersection 35 is arranged on the side of the hub 13 of the bristle carrier 11 close to the mounting tube 2. A distance d2 exists between the axis 28 and the axis 14.

In operation of the electric toothbrush, the third embodiment results in curve-shaped spatial motions of the free ends of the bristles 15 which differ from the spatial motions of the first and second embodiment, respectively.

Furthermore, the pin 23 and the slot 24 according to the first embodiment are absent in the third embodiment of FIG. 5. Instead, the third embodiment makes provision for a trunnion 37 which extends from the side of the plate 12 close to the mounting tube 2 approximately parallel to the transverse axis 14 in the direction of the mounting tube 2 and engages within an associated slot 38 in the mounting tube 2. Hence in the third embodiment the trunnion 37 and thereby the bristle carrier 11 are guided by the slot 38 in a way similar to the first embodiment in which the pin 23 is guided by the slot 24.

Preferably the angle formed by the longitudinal axis 3 and the angled end 19 of the shaft 7 is in a range of nearly 0 and 30 degrees, approximately.

To implement the guiding of the bristle carrier 11 with regard to the mounting tube 2, it will be understood that it is possible in all embodiments to substitute joints, flexible tension elements, metal springs, elastomeric members, etc. for a trunnion or the like engaging within a slot.

What is claimed is:

1. A brush section for an electric toothbrush, comprising a mounting tube in which a shaft rotatable mounted and driveable about a longitudinal axis is received, and a bristle carrier coupled to the shaft such that a rotary motion of the shaft about the longitudinal axis effects a rotary motion of the bristle carrier about a transverse axis that is transverse with respect to said longitudinal axis, wherein the bristle carrier is mounted directly on the shaft, and wherein the shaft is configured as a crankshaft having a first end and a second end, with the first end of the shaft providing the longitudinal axis while the second end of the shaft is arranged at an angle to the longitudinal axis.

2. The brush section as claimed in claim 1, wherein the angle has a value less than 30 degrees.

3. The brush section as claimed in claim 1 wherein the bristle carrier is pivotally mounted on said second angled end of the shaft.

4. The brush section as claimed in claim 1, 2 or 3 wherein said bristle carrier is constrained to move such that said transverse axis is movable within a plane that includes said longitudinal axis, and said transverse axis is movable about a pivot axis that is transverse to said plane, and wherein the longitudinal axis, the transverse axis, the second end of the shaft and said pivot axis pass through a common point of intersection.

5. The brush section as claimed in claim 1, 2 or 3 wherein said bristle carrier is constrained to move such that said transverse axis is movable within a plane that includes said longitudinal axis, and said transverse axis is movable about a pivot axis that is transverse to said plane, and wherein the longitudinal axis, the second end of the shaft and the pivot axis pass through a common point of intersection through which the transverse axis does not pass.

6. The brush section as claimed in claim 1 wherein a pin or a trunnion projects from the bristle carrier in the direction of the transverse axis and is coupled to a guiding structure that is connected to the mounting tube.

7. The brush section as claimed in claim 6, wherein the guiding structure is structure defining a slot or an opening which is provided in a cap structure affixed to the mounting tube or in the mounting tube itself and extends approximately parallel to the longitudinal axis, with the pin or the trunnion engaging said slot or opening.

8. The brush section as claimed in claim 1 or 3 wherein the shaft is adapted to be set in a continuous or an oscillatory rotational motion.

9. The brush section as claimed in claim 1 wherein means are provided which effect an additional pivotal motion of the bristle carrier about an axis extending at an angle of 90 degrees, approximately, to the transverse axis and the longitudinal axis.

10. The brush section as claimed in claim 2 wherein said angle is approximately ten degrees.

11. The brush section of claim 1 wherein said mounting tube and shaft are adapted to be push fit onto an electric tooth brush handle.

12. An electric toothbrush having a brush section comprising a mounting tube in which a shaft rotatable mounted and driveable about a longitudinal axis is received, and a bristle carrier coupled to the shaft such that a rotary motion of the shaft about the longitudinal axis effects a rotary motion of the bristle carrier about a transverse axis that is transverse with respect to said longitudinal axis, wherein the bristle carrier is mounted directly on the shaft, and wherein the shaft is configured as a crankshaft having a first end and a second end, with the first end of the shaft providing the longitudinal axis while the second end of the shaft is arranged at an angle to the longitudinal axis.

* * * * *